United States Patent [19]

Fink-Jensen

[11] Patent Number: 4,893,500

[45] Date of Patent: Jan. 16, 1990

[54] METHOD OF MEASURING THE FLOW PROPERTIES OF HIGH VISCOSITY FLUIDS AS WELL AS A DEVICE FOR CARRYING OUT THE INVENTIVE METHOD

[75] Inventor: Paul Fink-Jensen, Copenhagen, Denmark

[73] Assignee: Reciprotor A/S, Farum, Denmark

[21] Appl. No.: 246,508

[22] Filed: Sep. 19, 1988

[51] Int. Cl.[4] .......................................... G01N 11/10
[52] U.S. Cl. ...................................................... 73/60
[58] Field of Search ...................................... 73/54, 60

[56] References Cited

U.S. PATENT DOCUMENTS 4,155,250  5/1979  Dürner ..................................... 73/60
4,570,478  2/1986  Soong ..................................... 73/60

FOREIGN PATENT DOCUMENTS 2314671  2/1974  Fed. Rep. of Germany .
2310461  9/1974  Fed. Rep. of Germany .
2120793  12/1983  United Kingdom .

Primary Examiner—Stewart J. Levy
Assistant Examiner—Joseph W. Roskos
Attorney, Agent, or Firm—Scully, Scott, Murphy & Presser

[57] ABSTRACT

A method of measuring the flow properties of preferably high viscosity fluids, where a fluid is applied to a gap between a rod and a ring and subjected to a shear force by the mutual displacement of the ring and the rod, and where either the rod or the ring is imparted a controlled movement relative to the ring or the rod, respectively. Furthermore a device for carrying out the inventive method is provided. The device is of a size suitable for laboratory use and enables an improved temperature control as well as the determination of a complete flow curve in a single experiment.

12 Claims, 3 Drawing Sheets

METHOD OF MEASURING THE FLOW PROPERTIES OF HIGH VISCOSITY FLUIDS AS WELL AS A DEVICE FOR CARRYING OUT THE INVENTIVE METHOD

FIELD OF THE INVENTION

The present invention relates to a method of measuring the flow properties of preferably high viscosity fluids, where a fluid is applied to a gap between a rod and a ring and subjected to a shear force by the mutual displacement of the ring and the rod. Furthermore the invention relates to a device for carrying out the inventive method.

BACKGROUND ART

In the present connection high viscosity fluids mean fluids with a viscosity of approx. 1 Pa.sec. and above.

Most industrially used viscometers are rotation viscometers built in such a way that the viscosity of highly viscous fluids, such as offset ink, is only measurable at low shear rates. This is partially due to the often distinct visco-elastic properties of the fluids, and partially due to insufficient motor power. A further reason is that due to the heat generated during the measuring it is impossible to obtain a constant temperature of the fluid the viscosity of which is to be measured.

Examples of rotation viscometers for determining a flow curve are disclosed in DE-OS 2.310.461 and DE-AS 2.314.671.

It is also known to use viscosity measuring devices where a metal rod is moved downwards through a fixed ring and the fluid the viscosity of which is to be measured is applied to the inner side of said ring. The metal rod is subjected to different loads to determine correlated values for shear rates and shear stresses, cf. for instance DE-AS 2.754.075. The disadvantage when using such a rod viscometer is that in practice it is unavoidable for the rod to occasionally fall askew resulting in incorrect measurements. Moreover such a device can only determine one or a few measuring points on the flow curve by each measurement. Such a device is further disadvantageous in that the temperature is either impossible or very difficult to adjust and that the height of the device is necessarily at least twice the length of the rod.

GB specification no. 2.120.793 A discloses a viscometer for measuring the rheological properties of Newtonian fluids and Bingham plastics, where a control piston passes through a hollow cylinder comprising the fluid the viscosity of which is to be measured. The shear rate of the fluid in the gap between the piston and the cylinder, however, varies greatly between zero in the middle of the gap and a maximum at the limiting surfaces. Thus such a viscometer is in reality a specially constructed capillary viscometer and is thus unable to determine a flow curve where each measuring point derives from a well-defined, constant shear rate.

SUMMARY OF THE INVENTION

The object of the present invention is to provide a method and device for measuring the flow properties of preferably high viscosity fluids, said device being of a size rendering it suitable for laboratory use. The device enables an improved temperature control thus allowing the determination of a complete flow curve in a single experiment.

The object of the invention is accomplished by the inventive method, wherein either the rod or the ring is imparted a controlled movement relative to the ring or the rod, respectively. Thus the fluid is subjected to the desired variations in shear rate during a single experiment, said variations being for instance in the range of 0–4,000 sec$^{-1}$. At the same time the shear stress is measured concurrently (up to for instance 250 kPa), thus enabling the determination of a complete flow curve by a single experiment.

In a preferred inventive method the fluid is applied to the rod in form of a coating prior to performing the controlled movement. This ensures that the entire surface of the rod is covered so that insufficient coating of part of the surface with resulting air bubbles in the area of measurement is avoided.

Furthermore the present invention relates to a device for measuring the flow properties of preferably high viscosity fluids, said device comprising a rod and a ring movably borne around said rod, a gap being provided between the rod and the ring for receiving the fluid the viscosity of which is to be measured, said device further comprising a first measuring unit for measuring the shear force imparted to the fluid by the mutual displacement of the rod and the ring, and a second measuring unit for measuring the relative velocity of the ring and the rod, wherein the device comprises moving means for imparting a controlled movement to either the rod or the ring with respect to the ring or the rod, respectively. As a result a large amount of correlated values for shear rate (up to for instance 4,000 sec$^{-1}$) and shear stress (up to for instance 250 kPa) are measurable in a very short period, i.e. within a few seconds. Thus a complete flow curve or other characteristics can be automatically recorded within a short period of approx. 15 sec or less.

In a preferred embodiment of the inventive device the rod is stationary and the moving means comprises a threaded rod driven by a motor and extending parallel to the rod and co-operating with a nut-like member screwed onto the threaded rod and connected with the ring. The stationary rod enables a controlled movement in a device being of a size suitable for laboratory purposes simultaneous with a continuous measuring of the shear force (shear stress). This is to be seen with respect to, for instance, the device with mobile rod disclosed in DE-AS 2.754.075, where the force employed is obtained by using weights which can be removed individually or in groups during the movement of the rod.

In an especially preferred embodiment of the inventive device the nut-like member is connected with the ring via a universal joint. As a result the ring can center itself thus ensuring a uniform shear rate in the measuring area as well as reduced wear. At the same time a constant temperature is easily maintained.

In a further preferred embodiment of the inventive device the rod and inner surface of the ring form a cylindrical surface of rotation, thus facilitating the cleaning of the device.

In yet another preferred embodiment of the inventive device the passage forming a gap through the ring comprises a cylindrical area, each end of said area being connected with a coaxial area with increasing cross-section in the direction away from the cylindrical area. This is an especially suitable embodiment of the invention improving the self-centering effect.

In yet a further embodiment of the inventive device the gap is of a width of less than 200 μm, preferably of less than 100 μm. The use of such narrow gaps allows a comparatively low relative velocity between the rod and the ring while at the same time obtaining much higher shear rates than the ones obtained with known devices. Simultaneously the temperature increase of the material is reduced. This results in a decrease of the required length of the rod. Occuring acceleration phenomena, if any, become also less pronounced. On the other hand the gap is to be sufficiently large as to ensure that a possible inhomogenity of the fluid, for instance in connection with measuring the viscosity of pigmented materials, does not impede the measurement. Due to the narrow gap the necessary sample amount is small, i.e. in the order of approx. 1 g.

In a further preferred embodiment of the inventive device the rod is hollow and comprises a temperating fluid. Thus the temperature of the fluid the viscosity of which is to be measured is essentially constant. At the same time said temperature is known, a feature which for instance cannot be obtained by viscometers with movable rod.

Finally, in a preferred embodiment of the inventive device the first measuring unit comprises a weighing means to determine the shear force and thus the shear stress the fluid is subjected to.

BRIEF DESCRIPTION OF THE DRAWINGS

The invention is described in greater detail below with reference to the accompanying drawings, in which.

DESCRIPTION OF THE PREFERRED EMBODIMENT

Figure 1:
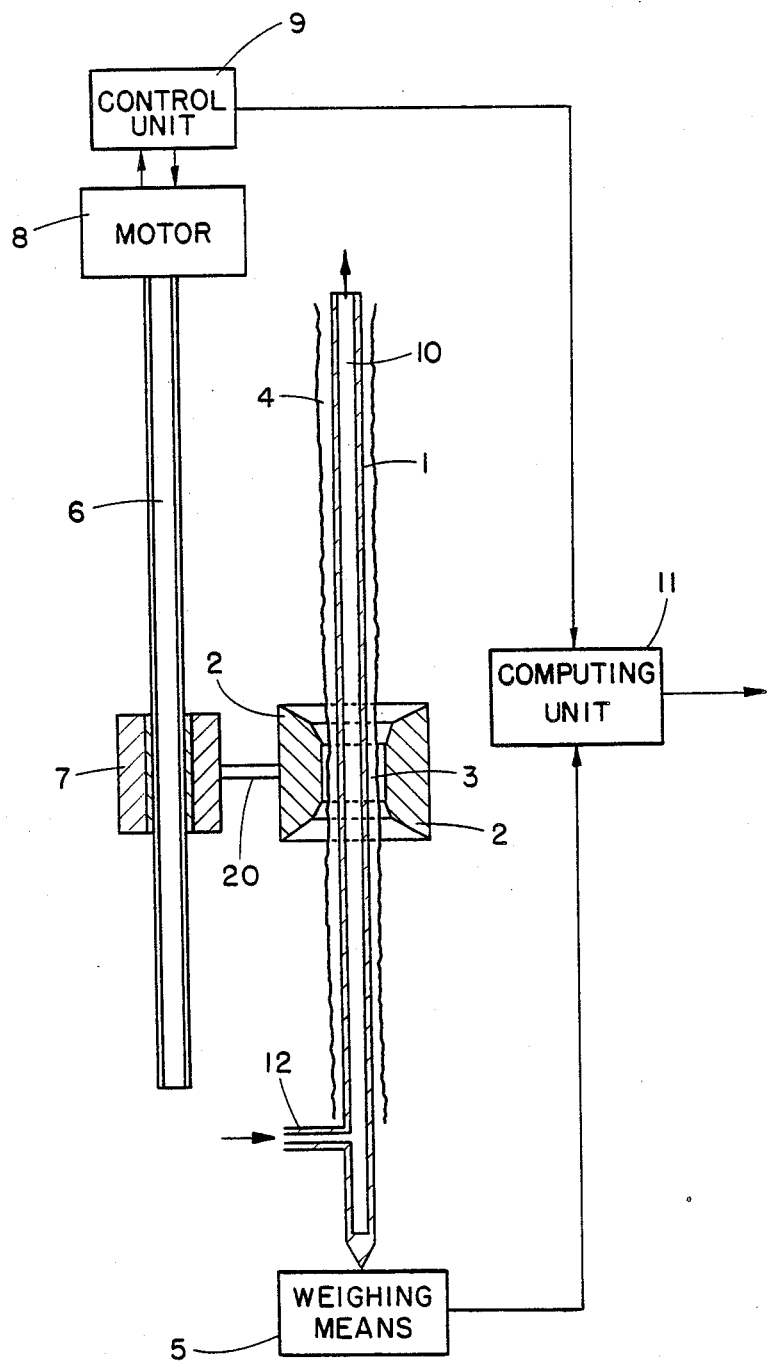
FIG. 1 is a diagrammatic view of an inventive device.
Figure 1A:
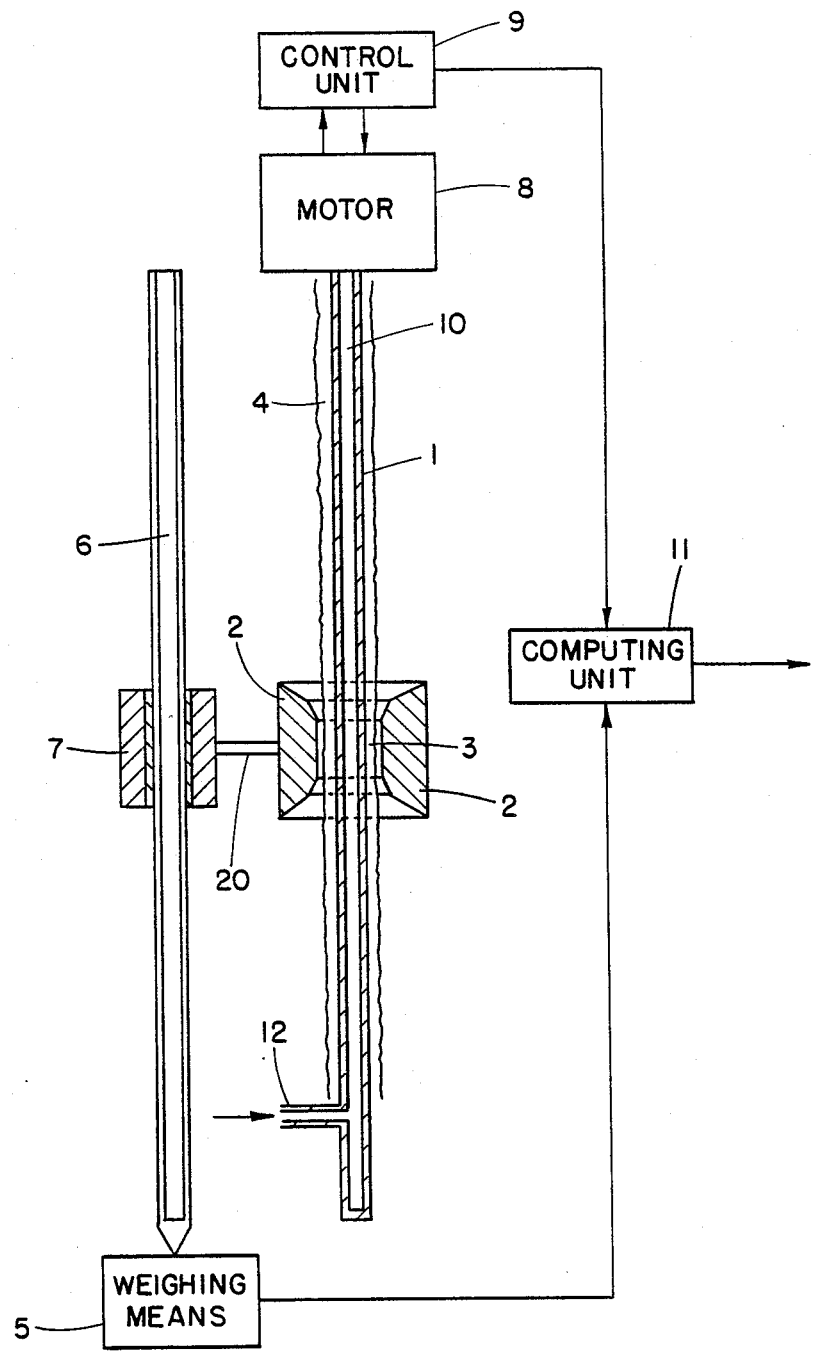
FIG. 1a is a diagrammatic view of another embodiment of the inventive device.

FIG. 1 illustrates an inventive device comprising a rod 1 as well as a ring 2 movably borne around said rod. Between the ring 2 and the rod 1 is a gap 3 shown exaggeratedly large in the drawing. The rod 1 is hollow and communicates with an input pipe 12 and an output pipe (not shown) for a suitable temperating fluid 10, preferably water, for providing a predetermined temperature. The lower end of the rod 1 is connected to a weighing means 5 emitting signals to a computing unit 11.

The inner side of the ring 2 is defined by a cylindrical area, each end of said area being connected with a coaxial area with increasing conicity.

The ring 2 is connected to a nut-like member 7 by means of a universal joint, as indicated at 20, ensuring that the ring is constantly automatically centered around the rod 1 when the device is in operation. The nut-like member 7 is moved along a threaded rod 6 by turning said threaded rod by means of a motor 8 and a control unit 9, the latter enabling a controlled movement of the nut-like member 7. The control unit 9 partly controls the predetermined speed as well as the predetermined acceleration and deceleration of the motor and partly measures at which speed the motor actually imparts the controlled movement to the nut-like member 7 and thus to the ring 2.

During operation the fluid the viscosity of which is to be measured is applied to the surface of the rod 1 in form of a layer. In practice the fluid is applied to the rod 1 at a level below the ring while the latter is in its top position. Then the ring is once moved slowly to the bottom end of the rod and back again. The fluid layer 4 and the gap 3 are adapted with respect to each other in such a way that the fluid layer is in contact with the ring all around the rod both at the inner cylindrical surface of the ring and at a part of the conical surface(s), against which the fluid layer is affected when moving the ring 2. For the sake of clarity the fluid layer 4 is shown too thin in the drawing. The nut-like member 7, the threaded rod 6 and the motor 8 cause the ring 2 to move with a velocity adjustable by the control unit 9. The controlled velocity is communicated in form of a velocity signal to the computing unit 11 also receiving the measured shear stresses measured at the weighing means 5, as noted above. Thus the relationship between shear stress and shear rate can be recorded, for instance in form of a flow curve.

The temperating fluid 10 ensures that the fluid 4 in the gap 3 is of a predetermined temperature at any given moment.

Figure 2:
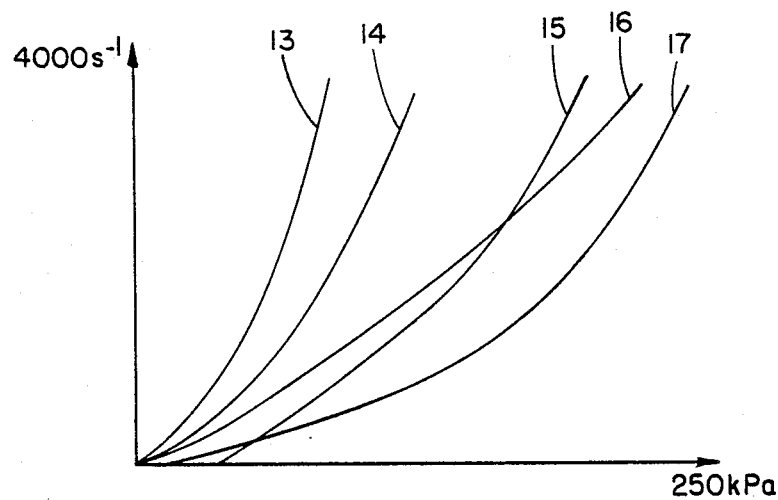
FIG. 2 illustrates various flow curves.

FIG. 2 illustrates diagrammatically examples of flow curves, drawn on the basis of correlated values of shear stress and shear rate measured by the inventive device. The curves 13-17 each show examples of a flow curve determined in a single experiment, while with known devices several experiments have to be conducted to obtain such flow curves.

The invention is described by means of a preferred embodiment of the inventive device. Modifications and alterations can, however, be made without thereby deviating from the scope of the invention. A conventional, commercially available ball nut with a threaded spindle can be used as the nut-like member with corresponding threaded rod.

I claim:

1. A device for measuring the flow properties of preferably high viscosity fluids, said device comprising a rod and a ring movably borne around said rod, a gap being provided between the rod and the ring for receiving the fluid whose viscosity is to be measured, said device further comprising a first measuring unit for measuring the shear force imparted to the fluid by the mutual displacement of the rod and the ring, and a second measuring unit for measuring the relative velocity of the ring and the rod, wherein moving means are provided for imparting a controlled movement to the ring with respect to the the rod.

2. A device as claimed in claim 1, wherein the rod is stationary and the moving means comprises a threaded rod driven by a motor and extending parallel to the rod and cooperating a nut-like member screwed on to the threaded rod and connected with the ring.

3. A device as claimed in claim 1, wherein the nut-like member is connected with the ring via a universal joint.

4. A device as claimed in claim 1, wherein the rod and inner surface of the ring form a cylindrical surface of rotation.

5. A device as claimed in claim 1, wherein a passage forming a gap through the ring comprises a cylindrical area, each end of said area being connected with a coaxial area with increasing cross-section in the direction away from the cylindrical area.

6. A device as claimed in claim 1, wherein the gap is of a width less than 200 um, preferably less than 100 um.

7. A device as claimed in claim 1, wherein the rod is hollow and comprises a temperating fluid.

8. A device as claimed in claim 1, wherein the first measuring unit comprises a weighing means.

9. A device for measuring the flow properties of preferably high viscosity fluids, said device comprising a rod and a ring movably borne around said rod, a gap being provided between the rod and the ring for receiving the fluid whose viscosity is to be measured, said device further comprising a first measuring unit for measuring the shear force imparted to the fluid by the mutual displacement of the rod and the ring, and a second measuring unit for measuring the relative velocity of the ring and the rod, wherein moving means are provided for imparting a controlled movement to the rod with respect to the ring.

10. A device as claimed in claim 9, wherein the ring is stationary and the moving means comprises a motor and said rod being provided with threads, said ring being secured to a nut-like member which is secured to a control rod.

11. A method of measuring the flow properties of preferably high viscosity fluids, comprising:

applying a fluid in the form of a coating to a gap between a rod and ring assembly;

subjecting said rod and ring to a shear force by displacing said ring relative to said rod; and measuring said flow properties of said fluid;

wherein said ring is displaced by imparting a controlled movement to said ring relative to said rod, said rod being stationary.

12. A method of measuring the flow properties of preferably high viscosity fluids, comprising:

applying a fluid in the form of a coating to a gap between a rod and a ring assembly;

subjecting said rod and ring to a shear force by displacing said rod relative to said ring; and measuring said flow properties of said fluid;

wherein said rod is displaced by imparting a controlled movement to said rod relative to said ring, said ring being stationary and secured to a control rod.

* * * * *